(12) United States Patent
Phillips et al.

(10) Patent No.: US 10,492,886 B2
(45) Date of Patent: Dec. 3, 2019

(54) INK FOR MARKING A TISSUE SPECIMEN

(71) Applicants: Janet L. F. Phillips, Oconomowoc, WI (US); Vector Surgical, LLC, Waukesha, WI (US)

(72) Inventors: Janet L. F. Phillips, Oconomowoc, WI (US); Scott E. Moore, Howell, MI (US)

(73) Assignee: VECTOR SURGICAL, LLC, Waukesha, WI (US)

( * ) Notice: Subject to any disclaimer, the term of this patent is extended or adjusted under 35 U.S.C. 154(b) by 237 days.

(21) Appl. No.: 15/313,378

(22) PCT Filed: Jun. 17, 2016

(86) PCT No.: PCT/US2016/038088
§ 371 (c)(1),
(2) Date: Nov. 22, 2016

(87) PCT Pub. No.: WO2016/205657
PCT Pub. Date: Dec. 22, 2016

(65) Prior Publication Data
US 2017/0189135 A1    Jul. 6, 2017

Related U.S. Application Data

(60) Provisional application No. 62/182,153, filed on Jun. 19, 2015.

(51) Int. Cl.
*C09D 11/00* (2014.01)
*C09D 11/54* (2014.01)
(Continued)

(52) U.S. Cl.
CPC ............. *A61B 90/90* (2016.02); *A61B 90/92* (2016.02); *C09D 11/00* (2013.01); *C09D 11/54* (2013.01); *G01N 1/28* (2013.01); *G01N 1/30* (2013.01)

(58) Field of Classification Search
None
See application file for complete search history.

(56) References Cited

U.S. PATENT DOCUMENTS 5,098,479 A    3/1992   Hutter
5,976,677 A   11/1999   Umeda et al.
(Continued)

FOREIGN PATENT DOCUMENTS

CN    101306943 A    11/2008
CN    103278649 A     9/2013
(Continued)

OTHER PUBLICATIONS

"Conversion between Stormer Viscometer Krebs Units and Viscosity Cup Drain Time"; Paul N. Gardner Company, Inc.; Jan. 1999; https://gardco.com/stormer_krebsconv_PU-G271.pdf; 4 pages.*
(Continued)

*Primary Examiner* — Helene Klemanski
(74) *Attorney, Agent, or Firm* — Fox Rothschild LLP

(57) ABSTRACT

An ink composition for marking a tissue specimen is provided. The ink composition has a general formula of 30.0 wt. % to 54.0 wt. % of an alkali soluble styrene; 0.3 wt. % to 1.7 wt. % ethyl hydroxyethyl cellulose; 8.0 wt. % to 35.0 wt. % colorant; 0.0 wt. % to 13.0 wt. % pigment; 23.0 wt. % to 47.0 wt. % deionized water; 0.35 wt. % to 1.65% defoamer and 0.1 wt. % to 1.1 wt. % preservative. The inks in accordance with the invention may have a peak transmission in the visible spectrum at a wavelength of from 322 nm to 716 nm or having a lineal UV-Vis spectrum with no visible peak transmission between 250 nm and 950 nm. When applied to a tissue specimen the ink compositions do not bleed onto adjacent tissue margins. When view under a microscope the color of the ink compositions can be distinguished from each other.

33 Claims, 8 Drawing Sheets

(51) Int. Cl.
*A61B 90/90* (2016.01)
*A61B 90/92* (2016.01)
*G01N 1/28* (2006.01)
*G01N 1/30* (2006.01)

(56) References Cited

U.S. PATENT DOCUMENTS

| | | | |
|---|---|---|---|
| 6,090,196 | A | 7/2000 | Babler |
| 6,657,003 | B2 | 12/2003 | Fox |
| 8,158,727 | B2 | 4/2012 | Onoe et al. |
| 8,750,966 | B2 | 6/2014 | Phillips et al. |
| 8,979,987 | B1 | 3/2015 | Stroud et al. |
| 9,044,268 | B2 * | 6/2015 | Phillips .................. A61B 90/39 |
| 2006/0090658 | A1 * | 5/2006 | Phillips .................. A61B 90/39 101/333 |
| 2008/0028962 | A1 * | 2/2008 | Phillips .................. A61B 90/39 101/333 |
| 2008/0121138 | A1 | 5/2008 | Kennedy et al. |
| 2010/0129550 | A1 | 5/2010 | Goddard et al. |
| 2012/0282311 | A1 | 11/2012 | Schmid et al. |
| 2015/0024324 | A1 | 1/2015 | Ota et al. |
| 2015/0094393 | A1 | 4/2015 | Holland et al. |
| 2017/0160174 | A1 * | 6/2017 | Ushida ..................... G01N 1/28 |

FOREIGN PATENT DOCUMENTS

| | | |
|---|---|---|
| CN | 103305053 A | 9/2013 |
| CN | 104335362 A | 2/2015 |
| EP | 2388567 A1 | 11/2011 |
| JP | 5035496 B2 | 9/2012 |
| WO | WO-2014062227 A1 | 4/2014 |

OTHER PUBLICATIONS

Canadian Office Action, issued by the Canadian Intellectual Property Office, regarding corresponding patent application Serial No. CA 2,989,996; dated Jan. 17, 2019, 6 pages.

Auschra, C. et al., The Role of Thickeners in Optimizing Coatings Formulation. [Retrieved from the internet Aug. 16, 2016] <http://www.chinacoatcongress.net/con2014_CD/Paper_EN/Paper_7_BASF_E.pdf>; 2014, p. 10, table 3 and second paragraph; p. 12, thrid paragraph; p. 13, figure 15.

Chroma-Chem, Products for Paint and Coatings. Apr. 2012; [Retrieved from the internet Aug. 16, 2016] ,<http://www.pcimag.com/ext/resources/VirtualBrochureFeb2012/Chromaflo.pdf?1372101688>. p. 43, col. 1, first paragraph; p. 44 table.

Kim, M_S et al.; An In Vivo Study of the Host Tissue Response to Subcutaneous Implantation of PLGA- and/or Porcine Small Intensine Submuscosa-based scaffolds. Biomaterials. vol. 28. Aug. 30, 2007; p. 5138, col. 2, second paragraph.

International Search Report and Written Opinion, issued by the ISA/U.S. Receiving Office, regarding corresponding international application Serial No. PCT/US2016/038088, dated Sep. 16, 2016, 18 pages.

* cited by examiner

INK FOR MARKING A TISSUE SPECIMEN

CROSS REFERENCE TO RELATED APPLICATIONS

This application is a national stage patent application of International patent application Serial No.: PCT/US2016/038088, filed on Jun. 17, 2016; which claims the benefit of U.S. Provisional patent application Ser. No. 62/182,153, filed on Jun. 19, 2015; the entireties of which are hereby incorporated by reference.

FIELD OF THE INVENTION

The present invention relates generally to ink that is useful in marking tissue specimens. In particular the invention relates to one or more inks and a fixing solution that are used to mark tissue specimens.

BACKGROUND OF THE INVENTION

When a surgeon removes cancerous tissue, it is carefully analyzed to estimate if any cancerous cells remain in the patient's body. The "tissue margin" is the edge or border of the tissue that has been removed during surgery; specific "margins" may refer to a subset of the exterior surface. A margin is designated as "clear" when no cancer cells are found at the tissue's edge. Conversely, a "positive" result is designated when cancer cells are found at the edge of the tissue, and the implication is that not all cancer was removed during surgery. In these cases, a second surgery or some other type of clinical treatment to address the remaining cancer cells may be recommended. Tissue specimens are evaluated in the pathology lab after surgery. For some types of surgery, such as breast cancer surgery, the excised tissue specimen is also evaluated by X-ray during the operation. The clinical status of the tissue margins is considered one of the most important factors in predicting whether there will be a recurrence of the cancer. The accurate identification and reporting of the clinical status of tissue margins (i.e., "clear of cancerous cells" or "positive for cancerous cells") is clinically relevant in a wide range of pathology specimens. Tissue marking inks are an important tool used in the determination of margin status and thereby affect the subsequent clinical action taken. Depending on the type of surgery, different colors of inks are used on a single specimen to designate: the specimen exterior surface margin; specific "margins" (or areas that are a subset of the entire specimen surface); particular anatomical features, or particular areas of concern on the specimen. Sometimes a "fixing solution" is applied after the inks to strengthen the adhesion of the ink to the tissue. Either before or after the ink is applied, the tissue is typically preserved in a "fixative" such as formalin. If the pathology analysis has a "positive" finding, the report informs the physician of the location in the patient's body where additional tissue should be removed or additional treatment directed.

A tissue specimen is often an irregular-shaped piece of tissue with fissures, crevasses or flaps on the surface. The tissue needs to be marked or labeled to designate the specimen margin(s) and original position of the tissue in the patient's body. The method of marking the tissue, which is typically to use ink, must mark accurately despite the irregularities in the surface of the specimen. If pathology analysis shows that cancerous cells are close to the exterior surface of the specimen, there may be additional cancerous cells remaining in the patient's body, requiring a subsequent surgery or other clinical treatment. For this subsequent surgery or clinical treatment to effectively address the any remaining cancer cells, it is essential that the original shape and location of the excised tissue is accurately determined. Inks that label the anatomy or the positioning of the excised tissue to indicate how it is originally positioned in the patient's body provide direction on where to target the subsequent surgery or treatment in order to more completely eradicate the cancer. Pathologists typically use inks to mark the exterior surfaces, or margins of excised tissue in cancer surgery. In some cases, the surgeon marks excised tissue before it is sent to the pathology lab.

Inks must adhere to tissue effectively for an accurate analysis in the pathology lab. They must dry quickly when applied to the tissue, both for the efficiency of use and also to maintain the fidelity of the markings without smearing or migrating on the tissue surface. The pathology lab makes slides of microscopic tissue specimens for analysis. Various materials and procedures are used to "process" the tissue specimen. The tissue is fixed, often using formalin; the pathologist then takes a slice of the tissue, typically approximately 5 microns thick, and places it on a glass slide. The slides are evaluated to identify the presence of cancerous cells, and the distance from the cancerous cells to the "margin," or the exterior of the specimen, is measured. A wider distance indicates that the cancerous cells are less likely to have spread beyond the boundaries of the excised tissue. A shorter distance suggests that there may be cancerous cells remaining in the patient's body, and a surgical re-excision or other clinical treatment to eradicate any remaining cancer is often performed. The success of this subsequent surgery or treatment may depend upon an accurate understanding of how the specimen was originally shaped and positioned in the patient's body, or the accurate identification of important anatomical features on the specimen. The location of the cancer cells that are close to the outer surface of the specimen or on a particular anatomical feature indicate the corresponding locations where remaining cancer cells may be present in the patient. Thus, it is critical that the ink that is applied to the surface of the tissue dries quickly and adheres securely, maintaining the integrity of the marking, without running, dripping or migrating to an adjacent area on the surface of the specimen or into a fissure or crevasse. If the ink does not dry quickly the fidelity of the markings are affected and the ink may smear or migrate on the tissue surface. If the ink migrates to an adjacent area on the surface of the tissue, and that area is determined to have cancerous cells close to the surface, then the surgical re-excision or clinical treatment directed at remaining cells in the patient may target the wrong location, resulting in untreated cancer cells which may cause a recurrence of the cancer. The most serious negative outcome is a local recurrence of the cancer. Of the 4% to 20% of lumpectomy patients who suffer a recurrence of their breast cancer, half of these cases are metastatic, or potentially deadly. If the ink migrates into a fissure or crevasse in the tissue, the pathology report may result in a "false positive," because the cancerous cells appear closer to the exterior surface of the tissue specimen than they actually were. A false positive could result in unnecessary surgery or clinical treatment for the patient. In breast cancer cases, re-excisions occur for up to 60% of lumpectomy patients, and of these, as many as 66% are false positives.

The viscosity of commercially available inks is widely variable. Thin inks often run and drip when applied to tissue, which prevents the accurate designation of specific tissue margins, which is the purpose for inking tissue. Moreover, thin inks have a great percentage of water and take a long time to dry. Thin inks can also run into crevasses of tissue, whereby the ink becomes closer to the cancer cells in the specimen, causing the margins to be misinterpreted, and creating a false positive result that may cause an unnecessary second surgery or treatment. On the other hand, thick inks can be lumpy and sometimes contain dry chards of crystallized matter, which appear to be microcalcifications (potentially cancerous cells) on the X-ray image taken during the surgical procedure. These dry fragments of ink may cause false positives in the interpretation of the X-ray image, resulting in unnecessary removal of additional tissue, or at a minimum causing confusion and delay during the operation while the patient is anesthetized.

Adherence to tissue can be problematic with commercially available inks when these inks are applied to tissue and the tissue is fixed in formalin. Tissue may be fixed in formalin before or after ink is applied. If tissue is fixed in formalin first, then the inks often adhere less effectively to the tissue. Commercially available inks do not adhere well to tissue that has been pre-fixed in formalin. If the inks are applied first and then the inked specimen is submerged into formalin, the inks may wash off of the tissue and into the formalin.

Commercially available inks are not sterile, which also results in problems. First, non-sterile inks may allow cross-contamination among tissue specimens because the applicator used to apply the ink may touch the specimen and then touch the bottle during the process of applying ink. Second, if the surgeon applies non-sterile inks while in the operating room, the non-sterile inks may not be used in the sterile field, which introduces the risk of errors if the specimen is carried across the room to the non-sterile area before it is inked or if inking is delayed until the surgery is complete. Third, non-sterile inks sometimes feature dry fragments that look like microcalcifications, or potentially cancerous cells, on the intraoperative X-ray image.

Other problems exist with commercially available inks. Although accurate identification of ink color is essential to effective clinical usage of the inks, the colors of commercially available inks are often difficult to distinguish from one another. To perform effectively, each ink color must be both recognizable and distinguishable from other colors under both reflective light (ordinary lighting conditions, as when the ink is applied to tissue in the pathology lab or operating room), and under transmitted light (when light shines through from the opposite side, as when the tissue on a slide is placed under a microscope). When the inks are viewed under reflective light, dark colors such as blue, violet and green are often difficult to distinguish from one another and all appear to be black. When applied to tissue and viewed on the slides under a microscope using transmitted light, difficulties are often encountered with the yellow-orange, orange-red, blue-violet and red-violet comparisons. Confusion accurately identifying the ink color on the specimen can lead to erroneous interpretation regarding the location of cells that are close to the specimen surface, resulting in re-excision or treatment in an incorrect location, and possibly cancer recurrence.

When inks are applied to tissue specimens, a fixing solution is sometimes used. The purpose of the fixing solution is to enhance the adherence of the inks to the tissue. However, commercially available fixing solutions are problematic in that they fail to effectively strengthen the adherence of the inks to the tissue, resulting in ink washing off when tissue is pre-treated with formalin before inking, submerged in formalin after ink is applied, or when a knife is used to cut through the inked specimen. In addition, some fixing solutions have an odor that is offensive to clinical staff.

Accordingly, there is a need for colored inks for marking tissue specimens that overcome the foregoing problems of commercially available inks. There is also a need for a fixing solution that prevents the wash-off of inks from the tissue specimens when the tissue is exposed to formalin before or after ink is applied.

BRIEF SUMMARY OF THE INVENTION

The problems outlined above are addressed by the ink for marking tissue specimens in accordance with the invention. The inks in accordance with the invention adhere well to a wide variety of tissue types, do not run, drip, bleed or smear onto adjacent tissue margins or into the interior of the specimen when the tissue is cut; adhere to tissue that has been previously fixed in formalin before ink is applied; adhere to tissue when the specimen is placed into formalin after inks are applied; have colors that are recognizable and distinct from other colors under both reflective light and transmitted light; are not detectable on an X-ray and do not leave artifacts that are visible on imaging, dry when applied to tissue within 2-3 minutes or less, and maintain color and performance characteristics when exposed to gamma radiation.

The foregoing is accomplished by ink compositions having a general formula of 30.0 wt. % to 54.0 wt. % of an alkali soluble styrene; 0.3 wt. % to 1.7 wt. % ethyl hydroxyethyl cellulose; 8.0 wt. % to 35.0 wt. % colorant; 0.0 wt. % to 13.0 wt. % pigment; 23.0 wt. % to 47.0 wt. % deionized water; 0.35 wt. % to 1.65% defoamer and 0.1 wt. % to 1.1 wt. % preservative. The inks in accordance with the invention may have a peak transmission in the visible spectrum at a wavelength of from 322 nm to 716 nm or having a lineal UV-Vis spectrum with no visible peak transmission between 250 nm and 950 nm.

Inks in accordance with the invention may be utilized to identify the orientation of a tissue specimen. The method of identifying the orientation of a tissue specimen having first, second and third surfaces includes providing at least three inks having three different colors each having a composition of 30.0 wt. % to 54.0 wt. % of an alkali soluble styrene; 0.3 wt. % to 1.7 wt. % ethyl hydroxyethyl cellulose; 8.0 wt. % to 35.0.0 wt. % colorant; 0.0 wt. % to 13.0 wt. % pigment; 23.0 wt. % to 47.0 wt. % deionized water; 0.35 wt. % to 1.65% defoamer and 0.1 wt. % to 1.1 wt. % preservative, said ink composition having properties that causes each of said at least three inks to adhere to the first, second and third surfaces of a tissue specimen, respectively, without bleeding into a crevice of the tissue specimen or onto an adjacent tissue margin.

The inks are also used with a novel fixing solution that overcomes the problems with conventional fixing solutions. The fixing solution has a formulation of from 31.0-35.0% ethanol (95%), 10.1-12.1% lactic acid, 31.3-35.3% deionized water and 21.0-23% formalin.

DETAILED DESCRIPTION OF THE INVENTION

As used herein the following terms have the definitions set forth next to them.

"Pigment" means the dry powder used to prepare and contained in a colorant or ink.

"Colorant" means a pigment dispersed in water with acrylic resin added.

"Ink" and "Ink Composition" means a colorant with the additional ingredients set forth herein, which is in final form and ready to be applied to tissue.

"Fixing solution" according to the invention described herein means a liquid mixture having a composition of from 31.0-35.0% ethanol (95%), 10.1-12.1% lactic acid, 31.3-35.3% deionized water and 21.0-23% formalin. The fixing solution enhances the adherence of the inks to the tissue.

"Fixative" means a colorless solution of formaldehyde in water (formalin) used to preserve biological specimens. Alternative "fixatives" include Weigners, Bouins, Hollandes, GreenFix, UPM, Cymol, Excell-Plus, FineFix, RCL2, HOPE, Glyo-Fixx, Cell-block.

Figure 1:
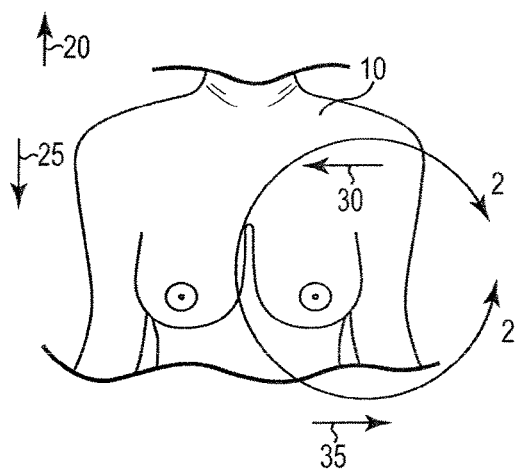
FIG. 1 is a front or anterior view of a patient including a tissue specimen to be removed from the patient.
Figure 2:
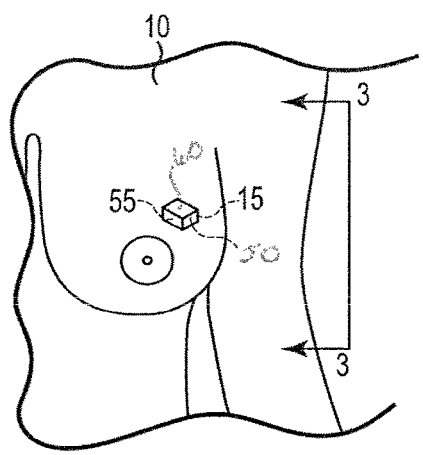
FIG. 2 is an enlarged front or anterior view of the portion of the patient and tissue specimen indicated at circle 2 of FIG. 1.
Figure 3:
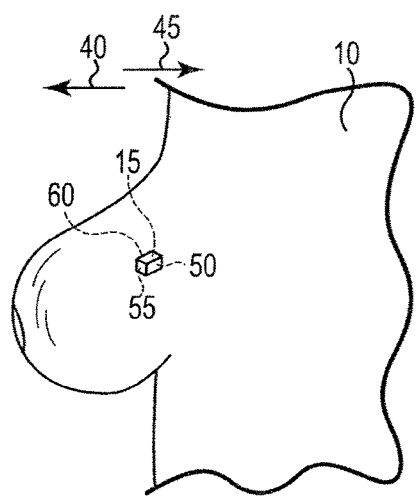
FIG. 3 is a side or lateral view of the portion of the patient and tissue specimen indicated at lines 3-3 of FIG. 2.

With reference to FIGS. 1-3, a patient 10 and a tissue specimen 15 are illustrated to show the tissue specimen's orientation in the patient 10. Before proceeding, it should be noted that the present invention will be described as it relates to a tissue specimen 15 removed from a breast. However, one of ordinary skill in the art will realize that the invention is applicable to many other types of tissue specimens in which tissue margin identification is important. In addition, those of skill in the art will appreciate that the inks and fixing solution in accordance with the invention may be used in both human subjects and animals.

For example, pancreatic cancer requires that a tissue specimen be removed, and that the original orientation and anatomical features be identified. As such, the invention should not be limited only to the uses described herein as it is well suited for use with any excised tissue that requires for pathology analysis designation of the specimen's: original orientation, the exterior margin surface or subsets of that surface, specific anatomical features, or particular areas of concern. These tissues include but are not limited to specimens of breast, pancreas, bone, thyroid, lymph nodes, brain, sarcomas, kidney, bowel, spleen, soft tissue masses, melanoma, squamous cell skin cancer, basal cell cancer, liver tumors, and the like.

FIG. 1 illustrates how the inks may be applied to a specimen to indicate the original orientation, or position, in the patient 10. For purposes of description, the direction 20 toward the patient's head will be identified as superior, while the opposite direction 25 is inferior. The direction 30 toward the patient's midline is defined as medial, while the opposite direction 35 is defined as lateral. With reference to FIG. 3, a side or medial view of a portion of the patient is shown to further illustrate orientation. The direction 40 toward the patient's front exterior is defined as anterior, while the opposite direction 45 is defined as posterior.

Figure 4:
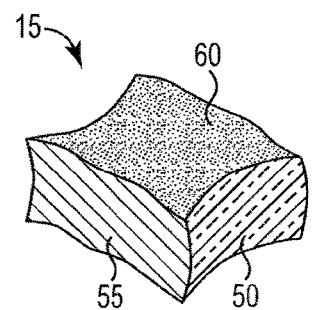
FIG. 4 is a perspective view of the tissue specimen of FIG. 1 after being removed from the patient of FIG. 1 showing three sides of the tissue that will be marked, in this case, superior, medial and lateral.

FIGS. 2 and 3 illustrate the tissue specimen 15 within the patient 10 prior to its removal, while FIG. 4 shows that same tissue specimen 15 after removal. With the specimen 15 still in the patient 10, the three surfaces 50, 55, 60 that will be marked can be seen. While any three planes or surfaces of the tissue specimen 15 can be used to identify the orientation of the specimen 15, it is preferred that at least three substantially orthogonal surfaces be identified, with some applications marking six or more surfaces. In FIGS. 2 and 3, the lateral surface 50, medial surface 55, and superior surface 60 of the tissue specimen 15 are shaded differently for illustrative purposes. In FIG. 4, the same three surfaces 50, 55, 60 are shaded to indicate that each one is marked with a different color.

Typically, to mark the surfaces 50, 55, 60, three different colored inks are employed. Ink colors in accordance with the invention include violet, green, blue, red, orange and yellow. However, those of skill in the art will appreciate that any color ink is contemplated to be within the scope of the invention so long as it meets the general formulation set forth in Table I.

Preferred ranges for the ink compositions in accordance with the invention are set forth in the Tables below. The inks in accordance with the invention have a viscosity of from 90 Krebs units (ku) to 115 ku and more preferably between 95 ku and 110 ku.

TABLE I

GENERAL INK FORMULATION

| Ingredient | Most Preferred Range | Preferred Range |
| --- | --- | --- |
| Alkali soluble styrene acrylic resin | 32.0-52.0 wt. % | 30.0-54.0 wt. % |
| Cellulose | 0.5-1.5 wt. % | 0.3-1.7 wt. % |
| Colorant (dispersed pigment) (available from Chromoflow Technologies, Somerset, NJ) | 10.0-33.0 wt. % | 8.0-35.0 wt. % |
| Pigment White Mica 6300 (available from A.E. Fleming, Warren, MI) | 0.0-12.0 wt. % | 0.0-13.0 wt. % |
| Deionized water | 25.0-45.0 wt. % | 23.0-47.0 wt. % |
| Amine | 0.05%-0.10% wt. % | 0.05-0.15 wt. % |
| Defoamer (BYK-011, BYK-012 or both) available from Altana AG: Wesel, Germany) | 0.5-1.5 wt. % | 0.35-1.65 wt. % |
| Preservative | 0.2-1.0 wt. % | 0.1-1.1 wt. % |

The ranges set forth above are critical to the inks in accordance with the invention. For example with respect to alkali soluble styrene acrylic resin, a composition having less than 30 wt. % will result in an ink that forms a brittle film on tissue with poor adhesion. A resin composition of more than 54.0 wt. % will result in an ink having poor or inadequate opacity, resulting in less visibility when applied to the tissue or on the slides. The inventors have found that in the claimed ink composition resin is one of the keys to superior adherence to tissue and fast drying on tissue, and is moisture resistant in an acidic atmosphere such as formalin. Notably, this composition is effective on fatty tissue, which is one of the most difficult tissue types on which to achieve adhesion. Examples of water-dispersible resins include synthetic resins such as polyester resins, polyurethane resins, polyepoxy resins, polyamide resins, polyether resins, poly (meth)acrylic resins, acryl-silicone resins, fluorine-based resins, polyolefin resins, polystyrene-based resins, polybutadiene-based resins, polyvinyl acetate-based resins, polyvinyl alcohol-based resins, polyvinyl ester-based resins, polyvinyl chloride-based resins, polyacrylic acid-based resins, unsaturated carboxylic acid-based resins and copolymers such as styrene-acrylate copolymer resins, styrene-butadiene copolymer resins, and combinations of the plural.

Preferred resins may be selected from DSM Neoresins, e.g. the NeoCryl product line, in particular acrylic styrene copolymer emulsions NeoCryl A-662, NeoCryl A-1131, NeoCryl A-2091, NeoCryl A-550, NeoCryl BT-101, NeoCryl SR-270, NeoCryl XK-52, NeoCryl XK-39, NeoCryl A-1044, NeoCryl A-1049, NeoCryl A-1110, NeoCryl A-1120, NeoCryl A-1127, NeoCryl A-2092, NeoCryl A-2099, NeoCryl A-308, NeoCryl A-45, NeoCryl A-615, NeoCryl BT-24, NeoCryl BT-26, NeoCryl BT-26, NeoCryl XK-15, NeoCryl X-151, NeoCryl XK-232, NeoCryl XK-234, NeoCryl XK-237, NeoCryl XK-238-NeoCryl XK-86, NeoCryl XK-90 and NeoCryl XK-95. Preferably NeoCryl A-2092 is used.

Similarly, an ink having a composition of less than 0.3 wt. % of cellulose will result in an ink having a low viscosity which in turn will lead to running and dripping on the tissue surface and migration into tissue crevices, resulting in inaccurate identification of tissue margins. Similarly, an ink having a cellulose composition of more than 1.7 wt. % will result in an ink having a viscosity higher than desirable, resulting in poor "transfer" capability. Poor transfer occurs when the ink is difficult to move in the process of loading it onto an applicator and then releasing it onto the tissue; adhesion to the tissue is problematic as well. Cellulose may be selected from ethyl hydroxyethyl cellulose or methyl ethyl hydroxyethyl cellulose and is preferably ethyl hydroxyethyl cellulose available as Bermocoll from Akzo Nobel N.V.: NL.

If the amount of colorant is less than 8.0 wt. % then the result is poor color differentiation when compared to other colors and poor correspondence between a particular color when viewed under reflective versus transmitted light. Conversely, if the amount of colorant is greater than 35.0 wt. % the resulting ink is brittle (when applied to tissue), resulting in distortion of the color under both reflective and transmitted light. In addition, the ink will have poor adherence to the tissue.

Water is an environmentally friendly and hence desirable solvent. In the present invention, the content of water to the whole ink composition is set forth in the Table above. An ink composition having less than 23.0 wt. % of water will be highly viscous and have poor transfer from the ink applicator to tissue. A water composition of more than 47 wt. % will result in an ink that is watery and has too low a viscosity, resulting in dripping, running, and migration when applied to tissue, resulting in the loss of fidelity between where the ink is applied and the ultimate interpretation of the margins. An additional result is poor "film build," or the thickness with which a layer of ink adheres to the tissue; poor film build compromises opacity, or the vividness with which the ink color is visible on the tissue.

Amine is added to the formula to help the cellulosic thickener activate and to adjust the pH to the desired range of approximately pH 8.5. If an ink has too little amine the resin will gel and lose its water solubility. If an ink composition has greater than 0.15 wt. % of amine, the pH of the system is too basic and it requires additional amounts of the fixing solution with an acidic pH to bring the pH below 7.0 so that the resin becomes insoluble. The insolubility of the resin is needed so that the ink does not bleed into the formalin solution.

With respect to a defoamer, an ink composition having less than 0.35 wt. % would be susceptible to foaming and lack viscosity stability, resulting in an apparent change in volume or density over time as the finished product is handled, shipped, or stored. For example, ink may completely fill a container upon packaging, but when the container is opened at a later date, the volume of ink may appear significantly reduced. An ink composition having a defoamer component greater than 1.65 wt. % would have irregularities (holes or weak spots in the coverage) because surface tension of the ink is too low. This may diminish the readability of the inks on the microscopic slides.

A preservative is used to prevent bacteria or mold growth in the inks. Preferable preservatives may be selected from the Euxyl line of products and include phenoxyethanol and ethylhexylglycerin available from Scheulke and Mayr (Norderstedt, Germany). A most preferable preservative is Euxyl PE-9010. The minimum amount of a preservative that is necessary is 0.1 wt. %. Consequences of an inadequate amount of preservative include bacteria and/or mold growth in the ink, which can distort the color under both reflective and transmitted light. For example, mold may appear as black spots in the ink under both reflective and transmitted light. Consequences of exceeding 1.1 wt. % of a preservative is an ink that has a low surface tension and uneven coverage on tissue.

In the ink composition of the present invention, a water-dispersible colorant is present. The ink composition may include one or more colorants and a pigment. It is critical that the colorants used in the inks in accordance with the invention be compatible with the resin system. In addition, each ink must be bright, recognizable, and easily distinguished from each different color of ink under both reflective and transmitted light, especially violet, green and black. Other critical ink characteristics include gloss and color "stability;" stability refers to the persistence of the color when exposed to acids or alkalis. Thus, the particular colorants selected for the inks in accordance with the invention achieve a balance between providing sufficient opacity to be distinguished visually when illuminated by both reflective light and transmitted light at various magnifications and exposures. Thus, the ink compositions in accordance with the invention have peak transmissions in the UV and visible spectrum at the wavelengths best seen FIGS. 5-6. White mica 6300 in amounts from 0.0-13.0 wt. % were added to the ink compositions to achieve the required brightness and color differentiation under reflected light. White mica 6300 increases the brightness of the colors under reflective light without occluding the transmitted light when viewed under the microscope. One may consider using $TiO_2$ as a brightener for reflective light; however, the inventors have found that TiO2 occludes the passage of light and creates a shadow, obscuring the ink color when viewed under transmitted light. Acceptable colorants are selected from the Plasticolors UCD-E line as noted below.

TABLE II

| Color | | Pigment - Colorants |
|---|---|---|
| Violet | White Mica 6300 | UCD 8406E Carbazole Violet (R-175) |
| Green | White Mica 6300 | UCD 5166E Phtahalo Green Yellow Shade (G-36) |
| Blue | White Mica 6300 | UCD 4820E Phthalo Blue Green Shade (BL 15-3) |
| Red | | UCD 7949E Naphthol Red (BS - R-170) plus UCD 8030E Quinacridone Red (V-19) |
| Orange | White Mica 6300 | UCD 5696E Benzimidazolone Yellow (Y-151) |

TABLE II-continued

| Color | | Pigment - Colorants |
|---|---|---|
| | | plus UCD 6012E Disazopyrazolone Orange (O-34) |
| Orange B | None | UCD 5696E Benzimidazolone Yellow (Y-151) plus UCD 6012E Disazopyrazolone Orange (O-34) plus UCD 6002E Orange 43 |
| Yellow | None | UCD 5696E Benzimidazolone Yellow (Y-151) |
| Black | None | UCD 1625E Lampblack (BK-7) |

Preferred ranges for the ink compositions in accordance with the invention are set forth in the Tables below. The color referenced below refers to the colorants identified in TABLE II above.

TABLE III

| | | VIOLET | | |
|---|---|---|---|---|
| Ingredient | | Most Preferable | More Preferable | Preferable |
| Resin | A2902 | 47.51 wt. % | 47.01 wt. % to 48.01 wt. % | 45.51 wt. % to 49.51 wt. % |
| Thickener | Cellulose | 1.00 wt. % | 0.90 wt. % to 1.10 wt. % | 0.80 wt. % to 1.20 wt. % |
| Colorant | Violet | 9.59 wt. % | 9.39 wt. % to 9.79 wt. % | 7.59 wt. % to 11.59 wt. % |
| Pigment | White Mica 6300 | 3.75 wt. % | 3.55 wt. % to 3.95 wt. % | 2.75 wt. % to 4.75 wt. % |
| Water | Deionized | 37.60 wt. % | 36.10 wt. % to 39.10 wt. % | 35.60 wt. % to 39.60 wt. % |
| Amine | AMP 95 | 0.05 wt. % | 0.05 wt. % to 0.10 wt. % | 0.05 wt. % to 0.15 wt. % |
| Defoamers | | 0.90 wt. % | 0.80 wt. % to 1.00 wt. % | 0.75 wt. % to 1.05 wt. % |
| Preservative | | 0.50 wt. % | 0.45 wt. % to 0.55 wt. % | 0.40 wt. % to 0.60 wt. % |

TABLE IV

| | | GREEN | | |
|---|---|---|---|---|
| Ingredient | | Most Preferable | More Preferable | Preferable |
| Resin | A2902 | 34.83 wt. % | 34.33 wt. % to 35.33 wt. % | 32.83 wt. % to 36.83 wt. % |
| Thickener | Cellulose | 0.70 wt. % | 0.60 wt. % to 0.80 wt. % | 0.50 wt. % to 0.90 wt. % |
| Colorant | Green | 26.48 wt. % | 25.98 wt. % to 26.98 wt. % | 24.48 wt. % to 28.48 wt. % |
| Pigment | White Mica 6300 | 9.60 wt. % | 9.10 wt. % to 10.10 wt. % | 8.60 wt. % to 10.60 wt. % |
| Water | Deionized | 27.06 wt. % | 25.56 wt. % to 28.56 wt. % | 25.06 wt. % to 29.06 wt. % |
| Amine | AMP 95 | 0.05 wt. % | 0.05 wt. % to 0.10 wt. % | 0.05 wt. % to 0.15 wt. % |
| Defoamer | | 0.90 wt. % | 0.80 wt. % to 1.0 wt. % | 0.75 wt. % to 1.05 wt. % |
| Preservative | | 0.50 wt. % | 0.45 wt. % to 0.55 wt. % | 0.40 wt. % to 0.60 wt. % |

TABLE V

| | | BLUE | | |
|---|---|---|---|---|
| Ingredient | | Most Preferable | More Preferable | Preferable |
| Resin | A2902 | 37.61 wt. % | 37.11 wt. % to 38.11 wt. % | 35.61 wt. % to 39.61 wt. % |
| Thickener | Cellulose | 0.75 wt. % | 0.65 wt. % to 0.85 wt. % | 0.55 wt. % to 0.95 wt. % |
| Colorant | Blue | 23.28 wt. % | 22.78 wt. % to 23.78 wt. % | 21.28 wt. % to 25.28 wt. % |
| Pigment | White Mica 6300 | 7.53 wt. % | 7.03 wt. % to 8.03 wt. % | 6.53 wt. % to 8.53 wt. % |
| Water | Deionized | 29.57 wt. % | 28.07 wt. % to 31.07 wt. % | 27.57 wt. % to 31.57 wt. % |
| Amine | AMP 95 | 0.05 wt. % | 0.05 wt. % to 0.10 wt. % | 0.05 wt. % to 0.15 wt. % |
| Defoamers | | 0.83 wt. % | 0.73 wt. % to 0.93 wt. % | 0.68 wt. % to 0.98 wt. % |
| Preservative | | 0.45 wt. % | 0.40 wt. % to 0.50 wt. % | 0.35 wt. % to 0.55 wt. % |

TABLE VI

| Ingredient | | Most Preferable | More Preferable | Preferable |
|---|---|---|---|---|
| | | RED | | |
| Resin | A2902 | 41.60 wt. % | 41.10 wt. % to 42.10 wt. % | 39.60 wt. % to 43.60 wt. % |
| Thickener | Cellulose | 0.83 wt. % | 0.73 wt. % to 0.93 wt. % | 0.63 wt. % to 1.03 wt. % |
| Colorant | UCD 7949E Naphthol Red (BS-R-170) | 17.18 wt. % | 16.83 wt. % to 17.53 wt. % | 15.18 wt. % to 19.18 wt. % |
| Colorant | UCD 8030E Quinacridone Red (V-19) | 6.40 wt. % | 6.30 wt. % to 6.50 wt. % | 4.40 wt. % to 8.40 wt. % |
| Water | Deionized | 32.70 wt. % | 31.20 wt. % to 34.20 wt. % | 30.70 wt. % to 34.70 wt. % |
| Amine | AMP 95 | 0.05 wt. % | 0.05 wt. % to 0.10 wt. % | 0.05 wt. % to 0.15 wt. % |
| Defoamers | | 0.91 wt. % | 0.81 wt. % to 1.01 wt. % | 0.76 wt. % to 1.06 wt. % |
| Preservative | | 0.45 wt. % | 0.40 wt. % to 0.50 wt. % | 0.35 wt. % to 0.55 wt. % |

TABLE VII

| Ingredient | | Most Preferable | More Preferable | Preferable |
|---|---|---|---|---|
| | | ORANGE | | |
| Resin | A2902 | 46.64 wt. % | 46.14 wt. % to 47.14 wt. % | 44.64 wt. % to 48.64 wt. % |
| Thickener | Cellulose | 0.96 wt. % | 0.86 wt. % to 1.06 wt. % | 0.76 wt. % to 1.16 wt. % |
| Colorant | UCD 5696E Benzimidazolone Yellow (Y-151) | 6.22 wt. % | 6.02 wt. % to 6.42 wt. % | 4.22 wt. % to 8.22 wt. % |
| Colorant | UCD 6012E Disazopyrazolone Orange (O-34) | 6.16 wt. % | 5.96 wt. % to 6.36 wt. % | 4.16 wt. % to 8.16 wt. % |
| Pigment | White Mica 6300 | 2.50 wt. % | 2.30 wt. % to 2.70 wt. % | 1.50 wt. % to 3.50 wt. % |
| Water | Deionized | 35.96 wt. % | 34.46 wt. % to 37.46 wt. % | 33.96 wt. % to 37.96 wt. % |
| Amine | AMP 95 | 0.05 wt. % | 0.05 wt. % to 0.10 wt. % | 0.05 wt. % to 0.15 wt. % |
| Defoamers | | 1.05 wt. % | 0.95 wt. % to 1.15 wt. % | 0.90 wt. % to 1.20 wt. % |
| Preservative | | 0.53 wt. % | 0.48 wt. % to 0.58 wt. % | 0.43 wt. % to 0.63 wt. % |

TABLE VIII

| Ingredient | | Most Preferable | More Preferable | Preferable |
|---|---|---|---|---|
| | | ORANGE B | | |
| Resin | A2902 | 42.95 wt. % | 42.45 wt. % to 43.45 wt. % | 40.95 wt. % to 44.95 wt. % |
| Thickener | Cellulose | 0.85 wt. % | 0.75 wt. % to 0.95 wt. % | 0.65 wt. % to 1.05 wt. % |
| Colorant | UCD 5696E Benzimidazolone Yellow (Y-151) | 11.79 wt. % | 11.59 wt. % to 11.99 wt. % | 9.79 wt. % to 13.79 wt. % |
| Colorant | UCD 6012E Disazopyrazolone Orange (O-34) | 2.36 wt. % | 2.16 wt. % to 2.56 wt. % | 0.36 wt. % to 4.36 wt. % |
| Colorant | UCD 6002E Orange 43 | 7.72 wt. % | 7.52 wt. % to 7.92 wt. % | 5.72 wt. % to 9.72 wt. % |
| Water | Deionized | 33.05 wt. % | 31.55 wt. % to 34.55 wt. % | 31.05 wt. % to 35.05 wt. % |
| Amine | AMP 95 | 0.05 wt. % | 0.05 wt. % to 0.10 wt. % | 0.05 wt. % to 0.15 wt. % |
| Defoamers | | 0.65 wt. % | 0.55 wt. % to 0.75 wt. % | 0.50 wt. % to 0.80 wt. % |
| Preservative | | 0.55 wt. % | 0.50 wt. % to 0.60 wt. % | 0.45 wt. % to 0.65 wt. % |

TABLE IX

| | | YELLOW | | |
|---|---|---|---|---|
| Ingredient | | Most Preferable | More Preferable | Preferable |
| Resin | A2902 | 39.45 wt. % | 38.95 wt. % to 39.95 wt. % | 37.45 wt. % to 41.45 wt. % |
| Thickener | Cellulose | 0.78 wt. % | 0.68 wt. % to 0.88 wt. % | 0.58 wt. % to 0.98 wt. % |
| Colorant | Yellow | 27.63 wt. % | 27.13 wt. % to 28.13 wt. % | 25.63 wt. % to 29.63 wt. % |
| Water | Deionized | 31.01 wt. % | 29.51 wt. % to 32.51 wt. % | 29.01 wt. % to 33.01 wt. % |
| Amine | AMP 95 | 0.05 wt. % | 0.05 wt. % to 0.10 wt. % | 0.05 wt. % to 0.15 wt. % |
| Defoamer | | 0.96 wt. % | 0.86 wt. % to 1.06 wt. % | 0.81 wt. % to 1.11 wt. % |
| Preservative | | 0.49 wt. % | 0.44 wt. % to 0.54 wt. % | 0.39 wt. % to 0.59 wt. % |

TABLE X

| | | BLACK | | |
|---|---|---|---|---|
| Ingredient | | Most Preferable | More Preferable | Preferable |
| Resin | A2902 | 44.88% | 44.38% to 45.38% | 42.88% to 46.88% |
| Thickener | Cellulose | 0.90% | 0.80% to 1.00% | 0.70% to 1.10% |
| Colorant | Black | 17.60% | 17.35% to 17.85% | 15.60% to 19.60% |
| Water | Deionized | 36.03% | 34.53% to 37.53% | 34.03% to 38.03% |
| Amine | AMP 95 | 0.05% | 0.00% to 0.10% | 0.00% to 0.10% |
| Defoamers | | 0.99% | 0.89% to 1.09% | 0.84% to 1.14% |
| Preservative | | 0.49% | 0.44% to 0.54% | 0.39% to 0.59% |

The following examples illustrate the preparation of the ink compositions in accordance with the invention.

Preparation of Ink Compositions

Example A

The method of preparing the ink compositions includes mixing two solutions, A and B. Solution A (Cellulose Thickener) is prepared using from 23.0 wt. % to 47.0 wt. % of deionized water and 0.3 wt. % to 1.7 wt. % of ethyl hydroxyethyl cellulose (Bermocoll EBM 5500—Akzo Nobel). The deionized water is added to a mixing vessel and the cellulose is gradually added to the water under agitation. A dispersion type blade, such as a Cowels disperser, is used for mixing. This solution can be mixed for approximately 20 to 35 minutes until smooth and lump free. From 0.05 wt. % to 1.05 wt. % of amino-2-methyl-1-propanol 95% active (5% water) (AMP 95—Angus Chemical) is then added and mixed into solution. After the solution thickens it is mixed further for 20-30 minutes. Mixing speed is increased as the thickening occurs. The speed of mixing is adjusted so that a vortex occurs in the solution. The solution is covered and allowed to sit for 5-12 hrs. or overnight at room temperature before mixing with Solution B.

Solution B, the final ink composition is then formed using the following materials:

| | |
|---|---|
| NeoCryl A 2092 Solution | 30.0-54.0 wt. % |
| Colorants | 8.0-35.0 wt. % |
| Mica | 0-13 wt. % |
| Defoamer | 0.35-1.65 wt. % |
| Preservative | 0.1-1.0 wt. % |

NeoCryl A 2092, the defoamers and Solution A, from above, are added to a mixing vessel and mixed until smooth and lump free with a dispersion blade. Colorant and a preservative are added under agitation while blending with a Cowels disperser. Mica may also be added depending on the ink composition. The solution is mixed for 10-15 minutes and the viscosity is checked. To achieve the desired viscosity, additional methyl ethyl hydroxyethyl cellulose (available as Bermocoll 5500 from AkzoNobel) may be added to the vortex under vigorous agitation until the viscosity of the solution reached is preferably between 90 Krebs units (ku) to 115 ku and more preferably between 95 ku and 110 ku. Viscosities are measured using a Brookfield KU-1 Viscometer. The solution is continued to be mixed for a minimum of an additional 20 minutes and the viscosity is measured again. When the desired viscosity of from 90 Krebs units to 115 Krebs units is reached, the solution is allowed to cool to room temperature. The resulting solutions are measured on an Agilant 8451 UV-Vis spectrophotometer and diluted until the violet, green, blue, red, orange, orange B and yellow ink compositions have a peak transmissions of from 322 nm to 716 nm.

Example B

A violet ink composition is prepared. Solution A (Thickener) is prepared using 35.60 wt. % of deionized water and 1.2 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. AMP 95 in an amount of 0.10 wt. % is then added and mixed into solution. After initial thickening of the solution, it is further mixed for 30 minutes, increasing the mixing speed as the thickening occurred. The speed of mixing is adjusted so that a vortex occurs in the solution. The solution is covered and allowed to sit for 7 hours at room temperature. Solution A is then added to a mixing vessel and mixed with 50.70 wt. % of NeoCryl A 2092 and 1.0 wt. % defoamer (BYK-012) with a Cowels dispersion blade until smooth and lump free. Added under agitation is 8.91 wt. % of carbazole violet 8406E and 2.49 wt. % of White Mica 6300 while blending using a Cowels disperser. The solution is mixed for 15 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 105 Krebs units and the solution is allowed to cool to room temperature. Violet ink prepared as illustrated above was measured on an Agilant 8451 UV-Vis spectrophotometer and diluted until the peak transmission shown in FIGS. 5 and 6 was produced. The violet ink composition had a peak transmission at 451 nm.

Example C

A violet ink composition is prepared. Solution A (Thickener) is prepared using 37.60 wt. % of deionized water and 1.0 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. AMP 95 in an amount of 0.05 wt. % is then added and mixed into solution. After initial thickening of the solution, it is further mixed for 30 minutes, increasing the mixing speed as the thickening occurs. The speed of mixing is adjusted so that a vortex occurs in the solution. The solution is covered and allowed to sit overnight at room temperature. Solution A is then added to a mixing vessel and mixed with 49.51 wt. % of NeoCryl A 2092 and 0.9 wt. % BYK-012 with a Cowels dispersion blade until smooth and lump free. Added under agitation is 7.91 wt. % of carbazole violet 8406E and 3.49 wt. % of white mica 6300 while blending using a Cowels disperser. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 95 Krebs units and the solution is allowed to cool to room temperature. Violet ink prepared as illustrated in this example was on an Agilant 8451 UV-Vis spectrophotometer and diluted until a peak transmission was obtained, shown in FIGS. 5 and 6. The violet ink composition had a peak transmission at 451 nm.

Example D

Figure 5:
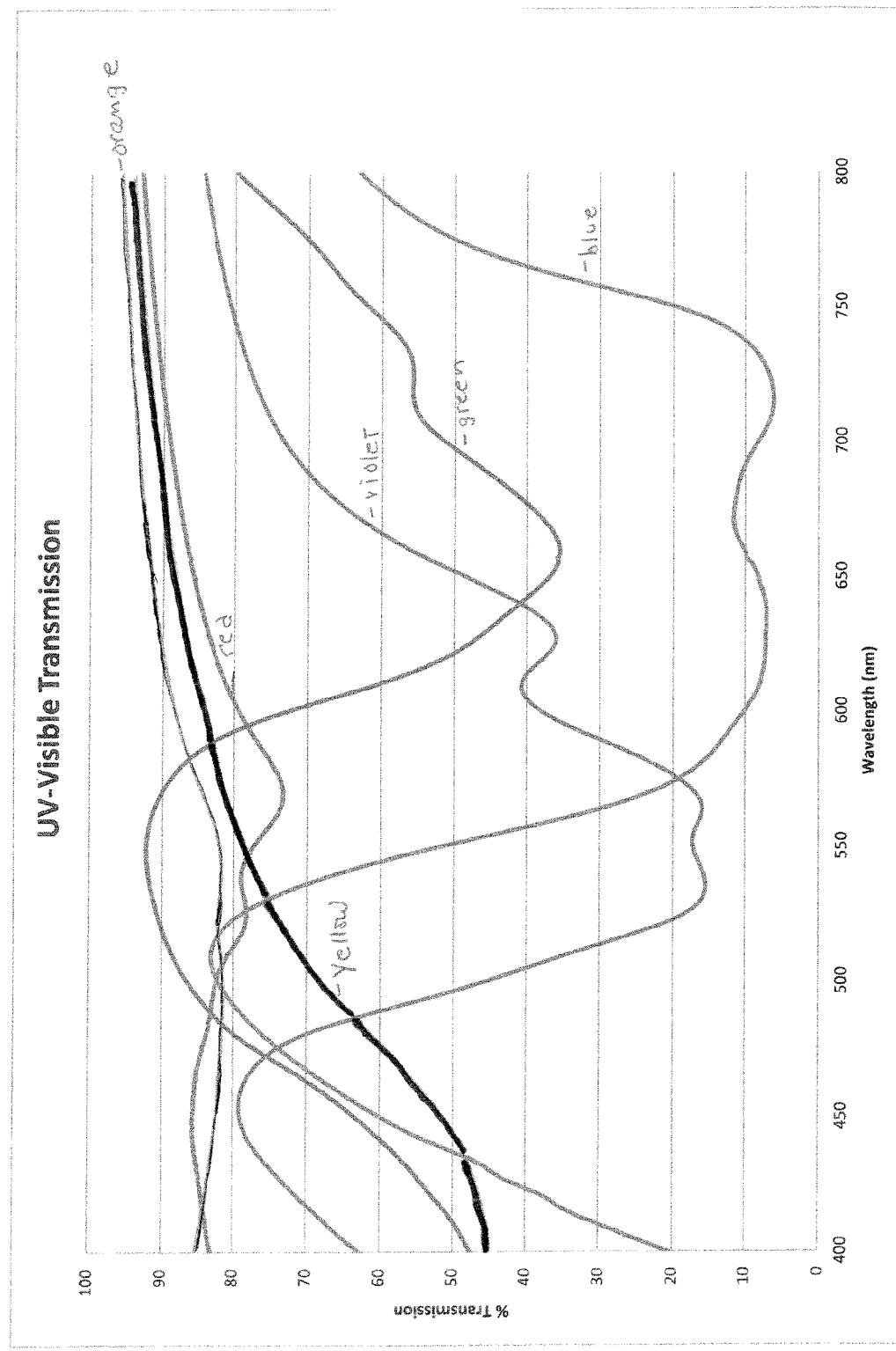
FIG. 5 is a graph from 400-800 nm depicting the light transmission characteristics of conventional inks.
Figure 6A:
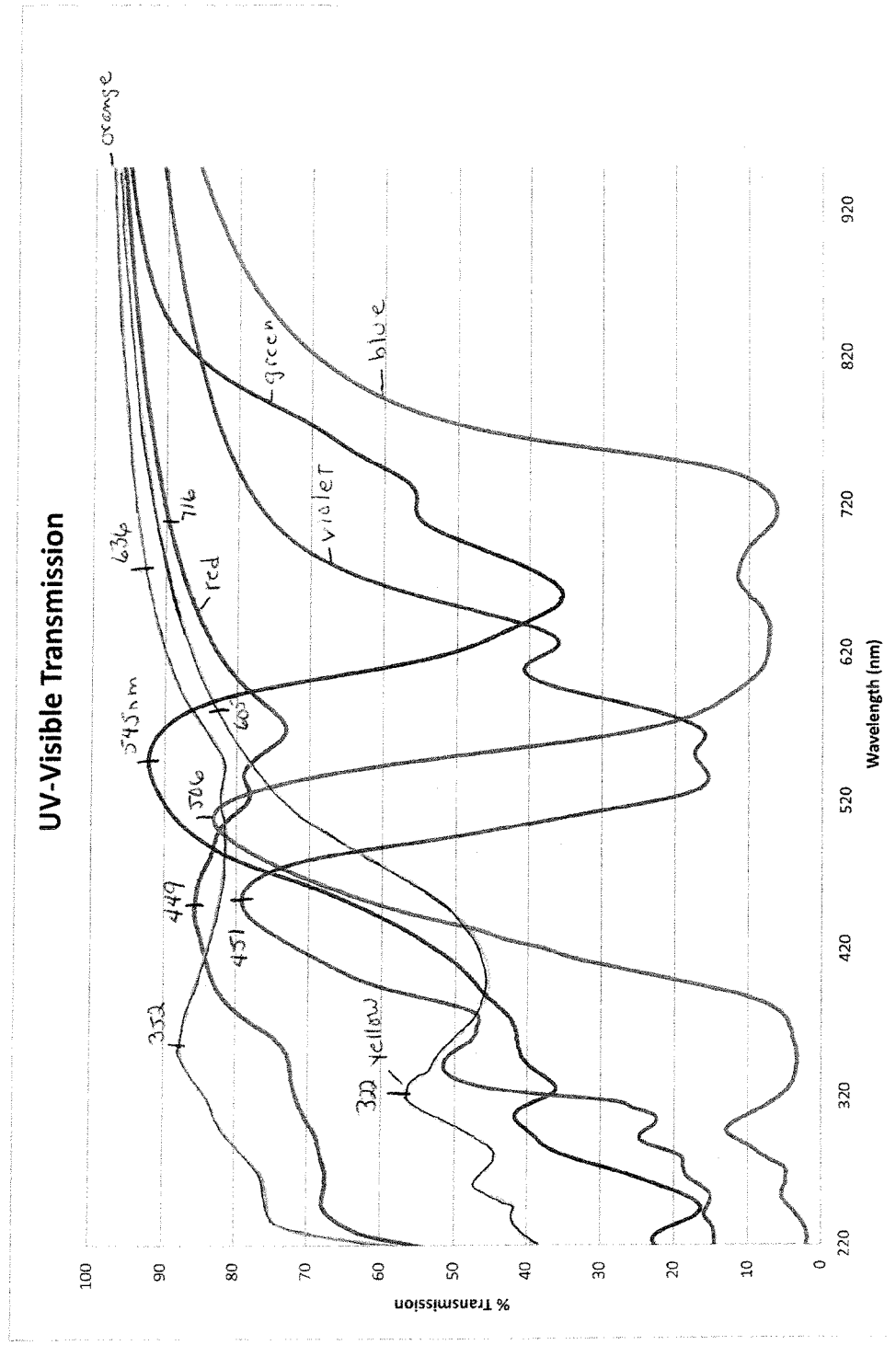
FIG. 6A is a graph from 220-920 nm depicting the light transmission characteristics of various ink composition in accordance with the invention.

A green ink is prepared using 25.61 wt. % of deionized water and 0.8 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. AMP 95 in an amount of 0.05 wt. % is then added and mixed into solution. After initial thickening of the solution, it is mixed for 30 minutes, increasing the mixing speed as it thickens until a vortex appeared in the solution. The solution is covered and allowed to sit at room temperature for five hours and is then added to a mixing vessel and mixed with 35.33 wt. % of NeoCryl A 2092 and 0.73 wt. % BYK-011 defoamer and blended with a Cowels dispersion blade until smooth and lump free. Pigments in the amounts of 26.98 wt. % of Phtahalo Green YS 5166E and 10.1 wt. % of white mica 6300 and 0.4 wt. % Euxyl PE-9010 were added under agitation while blending using a Cowels disperser. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 95 Krebs units and the solution is allowed to cool to room temperature. Green ink prepared as illustrated above was measured on an Agilant 8451 UV-Vis spectrophotometer and diluted until a peak transmission was, as shown in FIGS. 5 and 6, was obtained. The green ink composition had a peak transmission at 545 nm.

Example E

A green ink is prepared using 27.06 wt. % of deionized water and 0.7 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 30 minutes until smooth and lump free. AMP 95 in an amount of 0.05 wt. % is then added and mixed into solution. After initial thickening of the solution, it is mixed for 25 minutes, increasing the mixing speed as it thickens until a vortex appeared in the solution. The solution is covered and allowed to sit at room temperature for eight hours and is then added to a mixing vessel and mixed with 34.83 wt. % of NeoCryl A 2092 and 0.9 wt. % BYK-011 defoamer and blended with a Cowels dispersion blade until smooth and lump free. Added under agitation while blending with a Cowels disperser are 26.48 wt. % of Phtahalo Green YS 5166E and 9.6 wt. % of white mica 6300 and 0.5 wt. % Euxyl PE-9010. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 100 Krebs units and the solution is allowed to cool to room temperature. Green ink prepared as illustrated above was measured on an Agilant 8451 UV-Vis spectrophotometer and diluted until a peak transmission was, as shown in FIGS. 5 and 6, was obtained. The green ink composition had a peak transmission at 545 nm.

Example F

A blue ink composition is prepared using 29.57 wt. % of deionized water and 0.75 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. AMP 95 in an amount of 0.05 wt. % is then added and mixed into solution. After initial thickening of the solution, it is mixed for 30 minutes, increasing the mixing speed to compensate for the thickening of the solution until a vortex is in the solution. The solution is covered and allowed to sit at room temperature for five hrs. and is then added to a mixing vessel and mixed with 37.61 wt. % of NeoCryl A 2092 and 0.83 wt. % BYK-011 Defoamer and blended with a Cowels dispersion blade until smooth and lump free. Added under agitation while blending with a Cowels disperser are 23.28 wt. % of Phtahalo Blue GS 4820E and 7.53 wt. % of white mica 6300. A preservative in the amount of 0.45 wt. % of Euxyl PE-9010 is also added. The solution is mixed for 25 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 103 Krebs units and the solution is allowed to cool to room temperature. Blue ink prepared as illustrated in this example was measured on Agilant 8451 UV-Vis spectrophotometer and diluted until the peak transmission shown in FIGS. 5 and 6 was obtained. The blue ink composition had a peak transmission at 506 nm.

Example G

A blue ink composition is prepared using 31.57 wt. % of deionized water and 0.55 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 35 minutes until smooth and lump free. AMP 95 in an amount of 0.1 wt. % is then added and mixed into solution. After initial thickening of the solution, it is mixed for 30 minutes, increasing the mixing speed to compensate for the thickening of the solution until a vortex is in the solution. The solution is covered and allowed to sit at room temperature for seven hours and is then added to a mixing vessel and mixed with 38.94 wt. % of NeoCryl A 2092 and 0.68 wt. % BYK-011 Defoamer and blended with a Cowels dispersion blade until smooth and lump free. Added under agitation while blending with a Cowels disperser are 21.28 wt. % of Phtahalo Blue GS 4820E and 6.53 wt. % of white mica 6300. A preservative in the amount of 0.35 wt. % of Euxyl PE-9010 is also added. The solution is mixed for 25 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 110 Krebs units and the solution is allowed to cool to room temperature. Blue ink prepared as illustrated in this example was measured on Agilant 8451 UV-Vis spectrophotometer and diluted until the peak transmission shown in FIGS. 5 and 6 was obtained. The blue ink composition had a peak transmission at 506 nm.

Example H

A red ink composition is prepared using 32.70 wt. % of deionized water and 0.83 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. 0.05 wt. % AMP 95 is then added and mixed into solution. After initial thickening of the solution, it is mixed for 25 minutes, increasing the mixing speed to compensate for the thickening of the solution until a vortex is in the solution. The solution is covered and allowed to sit at room temperature for twelve hours and is then added to a mixing vessel and mixed with 41.6 wt. % of NeoCryl A 2092 and 0.91 wt. % BYK-012 defoamer and blended with a Cowels dispersion blade until smooth and lump free. Added under agitation while blending with a Cowels disperser are 17.18 wt. % of Naphthol Red 7949E and 6.4 wt. % Quinacridone Red 8030E. A preservative in the amount of 0.45 wt. % of Euxyl PE-9010 is also added. The solution is mixed for 30 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 110 Krebs units and the solution is allowed to cool to room temperature. Red ink prepared as illustrated in this example was measured on an Agilant 8451 UV-Vis spectrophotometer and diluted until the peak transmission shown in FIGS. 5 and 6 was obtained. The red ink composition had two peak transmissions at 449 nm and 716 nm.

Example I

A red ink composition is prepared using 34.70 wt. % of deionized water and 1.03 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free. 0.05 wt. % AMP 95 is then added and mixed into solution. After initial thickening of the solution, it is mixed for 25 minutes, increasing the mixing speed to compensate for the thickening of the solution until a vortex is in the solution. The solution is covered and allowed to sit at room temperature for six hours and is then added to a mixing vessel and mixed with 43.43 wt. % of NeoCryl A 2092 and 0.76 wt. % BYK-012 defoamer and blended with a Cowels dispersion blade until smooth and lump free. Added under agitation while blending with a Cowels disperser are 15.18 wt. % of Naphthol Red 7949E and 4.4 wt. % Quinacridone Red 8030E. A preservative in the amount of 0.45 wt. % of Euxyl PE-9010 is also added. The solution is mixed for 30 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 105 Krebs units and the solution is allowed to cool to room temperature. Red ink prepared as illustrated in this example was measured on an Agilant 8451 UV-Vis spectrophotometer and diluted until the peak transmission shown in FIGS. 5 and 6 was obtained. The red ink composition had two peak transmissions at 449 nm and 716 nm.

Example J

An orange ink composition is prepared using 35.96 wt. % of deionized water and 0.96 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 30 minutes until smooth and lump free and 0.05 wt. % AMP 95 is then added and mixed into solution. After initial thickening of the solution, it is mixed for an additional 25 minutes, increasing the mixing speed to compensate for the thickening of the solution until a vortex is in the solution. The solution is covered and allowed to sit at room temperature for twelve hours and is then added to a mixing vessel and mixed with 46.64 wt. % of NeoCryl A 2092 and 1.05 wt. % BYK-011 defoamer and blended with a Cowels dispersion blade until smooth and lump free. Added under agitation while blending with a Cowels disperser are 6.22 wt. % of Benzimidazolone Yellow 5696E, 6.16 wt. % Disazopyrazolone Orange 6012E and 2.5 wt. % White Mica 6300. Euxyl PE-9010 preservative in the amount of 0.53 wt. % is also added. The solution is mixed for 15 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 90 Krebs units and the solution is allowed to cool to room temperature. Orange ink prepared as illustrated in this example was measured on an Agilant 8451 UV-Vis spectrophotometer and diluted until the peak transmission shown in FIGS. 5 and 6 was obtained. The orange ink composition had two peak transmissions at 352 nm and 636 nm.

Example K

An orange ink composition is prepared using 37.96 wt. % of deionized water and 1.10 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 30 minutes until smooth and lump free and 0.10 wt. % AMP 95 is then added and mixed into solution. After initial thickening of the solution, it is mixed for an additional 25 minutes, increasing the mixing speed to compensate for the thickening of the solution until a vortex is in the solution. The solution is covered and allowed to sit at room temperature for twelve hours and is then added to a mixing vessel and mixed with 48.64 wt. % of NeoCryl A 2092 and 1.20 wt. % BYK-011 defoamer and blended with a Cowels dispersion blade until smooth and lump free. Added under agitation while blending with a Cowels disperser are 4.91 wt. % of Benzimidazolone Yellow 5696E, 4.16 wt. % Disazopyrazolone Orange 6012E and 1.5 wt. % White Mica 6300. Euxyl PE-9010 preservative in the amount of 0.43 wt. % is also added. The solution is mixed for 15 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 95 Krebs units and the solution is allowed to cool to room temperature. Orange ink prepared as illustrated in this example was measured on an Agilant 8451 UV-Vis spectrophotometer and diluted until the peak transmission shown in FIGS. 5 and 6 was obtained. The orange ink composition had two peak transmissions at 352 nm and 636 nm.

Example L

An orange ink composition is prepared using 33.05 wt. % of deionized water and 0.88% wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 30 minutes until smooth and lump free and 0.10 wt. % AMP 95 is then added and mixed into solution. After initial thickening of the solution, it is mixed for an additional 35 minutes, increasing the mixing speed to compensate for the thickening of the solution until a vortex is in the solution. The solution is covered and allowed to sit at room temperature overnight and is then added to a mixing vessel and mixed with 42.95% wt. % of NeoCryl A 2092 and 0.65 wt. % BYK-011 defoamer and blended with a Cowels dispersion blade until smooth and lump free. Added under agitation while blending with a Cowels disperser are 11.79% wt. % of Benzimidazolone Yellow 5696E, 2.36 wt. % Disazopyrazolone Orange 6012E and 7.72 wt. % Orange 43 6002E. Euxyl PE-9010 preservative in the amount of 0.55 wt. % is also added. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 90 Krebs units and the solution is allowed to cool to room temperature. Orange ink prepared as illustrated in this example is measured on an Agilant 8451 UV-Vis spectrophotometer and diluted until a peak transmission is obtained. It is predicted that the orange ink composition will have two peak transmissions between 450 nm and 675 nm.

Example M

An orange ink composition is prepared using 35.05 wt. % of deionized water and 0.65% wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 25 minutes until smooth and lump free and 0.10 wt. % AMP 95 is then added and mixed into solution. After initial thickening of the solution, it is mixed for an additional 30 minutes, increasing the mixing speed to compensate for the thickening of the solution until a vortex is in the solution. The solution is covered and allowed to sit at room temperature for seven hours and is then added to a mixing vessel and mixed with 44.95% wt. % of NeoCryl A 2092 and 0.5 wt. % BYK-011 defoamer and blended with a Cowels dispersion blade until smooth and lump free. Added under agitation while blending with a Cowels disperser are 12.22% wt. % of Benzimidazolone Yellow 5696E, 0.36 wt. % Disazopyrazolone Orange 6012E and 5.72 wt. % Orange 43 6002E. Euxyl PE-9010 preservative in the amount of 0.45 wt. % is also added. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 100 Krebs units and the solution is allowed to cool to room temperature. Orange ink prepared as illustrated in this example is measured on an Agilant 8451 UV-Vis spectrophotometer and diluted until a peak transmission is obtained. It is predicted that the orange ink composition will have two peak transmissions between 450 nm and 675 nm.

Example N

A yellow ink composition is prepared using 31.01 wt. % of deionized water and 0.78 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 20 minutes until smooth and lump free and 0.05 wt. % AMP 95 is then added and mixed into solution. After initial thickening of the solution, it is mixed for an additional 25 minutes, increasing the mixing speed as the solution thickens until a vortex is appears. The solution is covered and allowed to sit at room temperature for twelve hours and is then added to a mixing vessel and mixed with 39.45 wt. % of NeoCryl A 2092 and 0.96 wt. % BYK-012 defoamer and blended with a Cowels dispersion blade until smooth and lump free. Added under agitation while blending with a Cowels disperser is 27.63 wt. % of Benzimidazolone Yellow 5696E. Euxyl PE-9010 preservative in the amount of 0.49 wt. % is also added. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 95 Krebs units and the solution is allowed to cool to room temperature. Yellow ink prepared as illustrated in this example was measured on an Agilant 8451 UV-Vis spectrophotometer and diluted until the peak transmission shown in FIGS. 5 and 6 was obtained. The yellow ink composition had two peak transmissions at 322 nm and 605 nm.

Example O

A yellow ink composition is prepared using 33.0 wt. % of deionized water and 0.58 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 20 minutes until smooth and lump free and 0.05 wt. % AMP 95 is then added and mixed into solution. After initial thickening of the solution, it is mixed for an additional 25 minutes, increasing the mixing speed as the solution thickens until a vortex is appears. The solution is covered and allowed to sit at room temperature for twelve hours and is then added to a mixing vessel and mixed with 39.14 wt. % of NeoCryl A 2092 and 1.1 wt. % BYK-012 defoamer and blended with a Cowels dispersion blade until smooth and lump free. Added under agitation while blending with a Cowels disperser is 25.63 wt. % of Benzimidazolone Yellow 5696E. Euxyl PE-9010 preservative in the amount of 0.49 wt. % is also added. The solution is mixed for 20 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 115 Krebs units and the solution is allowed to cool to room temperature. Yellow ink prepared as illustrated in this example was measured on an Agilant 8451 UV-Vis spectrophotometer and diluted until the peak transmission shown in FIGS. 5 and 6 was obtained. The yellow ink composition had two peak transmissions at 322 nm and 605 nm.

Example P

Figure 6B:
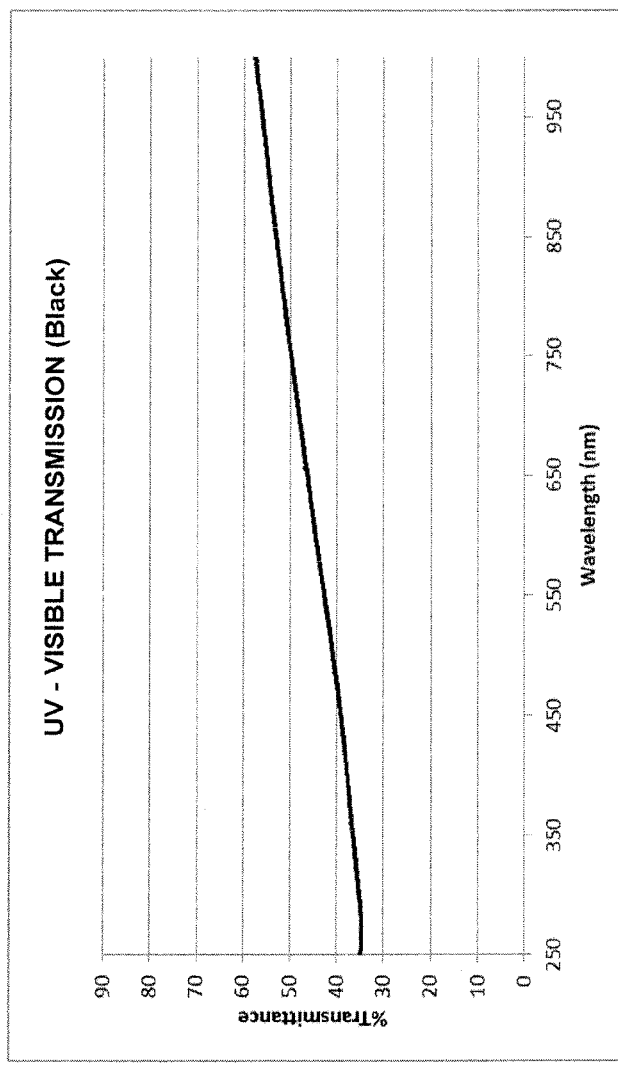
FIG. 6B is a graph from 250-950 nm depicting the light transmission characteristics of the black ink composition in accordance with the invention.
Figure 7:
FIGS. 7 and 8 are a visual depiction of how a commercially available ink drips and run into other adjacent ink when applied on tissue.
Figure 8:
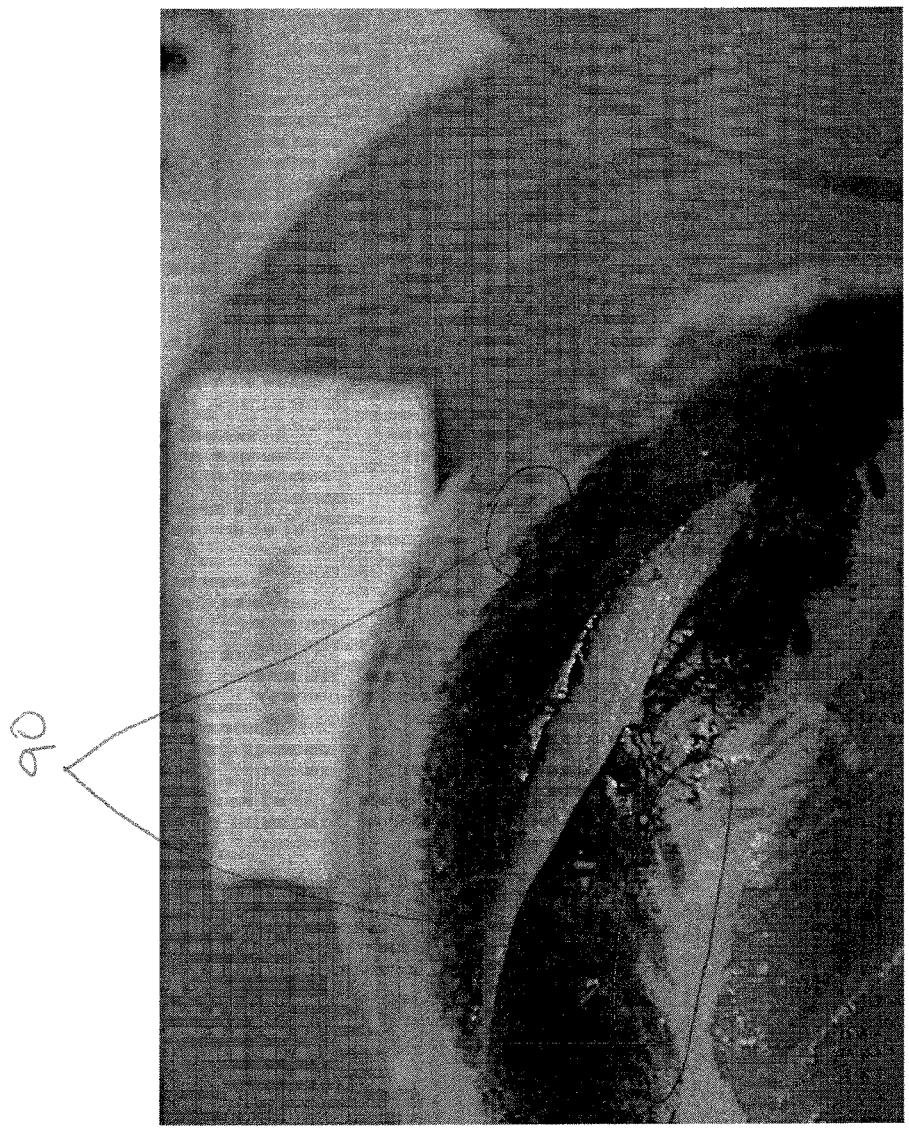
Figures 9A, 9B:
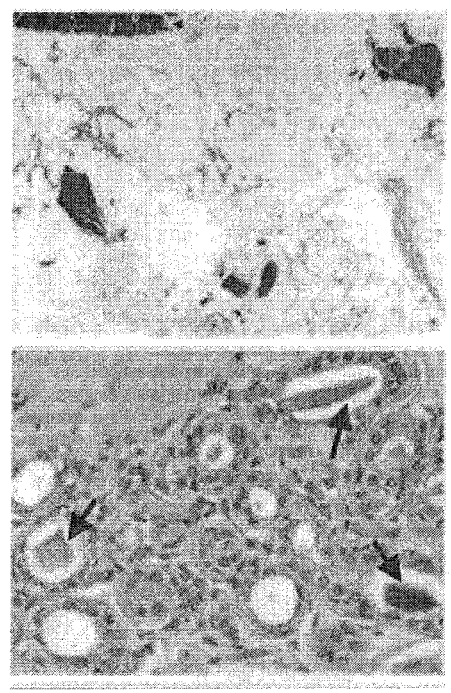
FIG. 9A is a radiograph of a tissue specimen depicting the histologic appearance of actual microcalcifications in the tissue.
FIG. 9B is a radiograph of a tissue specimen marked with commercially available ink showing the false appearance of a cluster of microcalcifications.

A black ink composition is prepared using 34.53 wt. % of deionized water and 0.8 wt. % of ethyl hydroxyethyl cellulose (Bermocoll EBM 5500—Akzo Nobel). The deionized water is added to a mixing vessel and the cellulose is gradually added to the water under agitation. A Cowels dispersion blade is used for mixing. The solution is mixed for 20 minutes until smooth and lump free and 0.02 wt. % AMP 95 is then added and mixed into solution. After initial thickening of the solution, it is mixed for an additional 25 minutes, increasing the mixing speed to compensate for the thickening of the solution until a vortex is in the solution. The solution is covered and allowed to sit at room temperature for ten hours and is then added to a mixing vessel and mixed with 44.38 wt. % of NeoCryl A 2092 acrylic resin and 0.90 wt. % BYK-012 defoamer and blended with a Cowels dispersion blade until smooth and lump free. Colorant in the amount of 17.85 wt. % of Lampblack 1625E is added under agitation while blending using a Cowels disperser. Euxyl PE-9010 preservative in the amount of 0.49 wt. % is also added. The solution is mixed for 15 minutes and the viscosity is checked. To achieve the desired viscosity, additional methyl ethyl hydroxyethyl cellulose (available as Bermocoll 5500 from AkzoNobel) may be added to the mixture under vigorous agitation. The viscosity is 108 Krebs units and the solution is allowed to cool to room temperature. As can be seen in FIG. 6B, the black ink prepared as illustrated in this example was measured on an Agilant 8451 UV-Vis spectrophotometer and produced a lineal UV-Vis spectrum having no visible peak transmission between 250 nm and 950 nm.

Reflective Light

All inks prepared as illustrated in Examples A through 0 were measured for reflective light in the L.a.b. color space on an X-Rite spectrophotometer. The L.a.b. color space is a color-opponent space with dimension L for lightness and a and b for the color-opponent dimensions, based on nonlinearly compressed (e.g. CIE XYZ color space) coordinates. The scale for dimensions "a" and "b" on the X-Rite spectrophotometer used was −100 to +100. In dimension "a" the higher the value, the redder the color and the lower the value the greener the color. In dimension "b" the higher the value the more yellow the color and the lower the value the more blue the color. Three separate measurements were taken on the inks prepared as illustrated in Examples A through P and the values averaged. The average values appear in Table XI below.

TABLE XI

| | Average L.a.b. | | |
|---|---|---|---|
| Color | L | a | b |
| Red | 40.80 | +49.29 | +28.89 |
| Orange | 57.24 | +52.04 | +44.62 |
| Orange B | 53.50 | +52.81 | +44.52 |
| Yellow | 84.51 | +6.63 | +88.09 |
| Green | 53.29 | −42.32 | +18.8 |
| Blue | 40.94 | −15.37 | −30.73 |
| Violet | 31.40 | +13.2 | −22.13 |
| Black | 25.81 | −0.02 | −0.49 |

Sterilization Procedure

All inks in accordance with the invention may desirably be sterilized. If sterilized via gamma radiation the inks in accordance with the invention maintain their key characteristics of adhering well to a wide variety of tissue types, having sufficient viscosity such that they do not run, drip, bleed or smear onto adjacent tissue margins or into the interior of the specimen when the tissue is cut; adhering to tissue that has been previously fixed in formalin before ink is applied; adhering to tissue when the specimen is placed into formalin after inks are applied; having colors that are recognizable and distinct from other colors under both reflective light and transmitted light; not being detectable on an X-ray and not leaving artifacts that are visible on imaging, and drying when applied to tissue within 2-3 minutes or less.

TABLE XII

| Target | Preferred Range | Acceptable Range |
|---|---|---|
| 33 kGy | 31.0 kGy-39 kGy | 27.5 kGy-45 kGy |

If the inks are subjected to gamma radiation of less than 27.5 kGy the ink may not be sterile. If the inks are subjected to gamma radiation more than 45 kGy the ink properties may be compromised, resulting in performance issues.

Gamma radiation comprises high-energy photons that are emitted from an isotope source (Cobalt 60) producing ionization (electron disruptions) throughout a product. Each lot of ink is sterilized within approximately one week of manufacturing. When processing each pallet is broken down and loaded into a tote of processing per the approved load diagram and a detailed run record is followed indicating what product, lot number and number of cases is to be loaded in each tote. The inks in accordance with the invention are subjected to a minimum specified dose of 27 kGy and a maximum specified dose of 45 kGy. The target dose, and most preferred dose is 33 kGy.

Example Q

Figure 10:
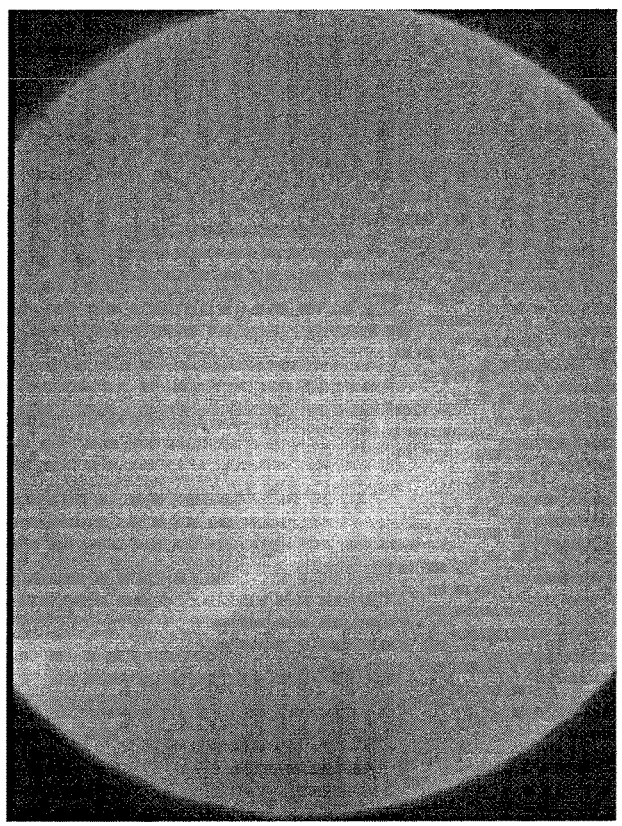
FIG. 10 is an X-ray of tissue marked with the ink in accordance with the present invention showing no appearance of calcifications.

Three inks chosen at random from ink prepared as illustrated in Examples A through P above were applied to six areas of a piece of tissue. The inks were applied to anterior, inferior, lateral, medial, posterior and superior surfaces. The inks dried within two to three minutes of application. When the specimen was X-rayed, the ink did not leave any artifacts that were visible on the image as best seen in FIG. 10. There was minimal to no leaching of the ink into the formalin when tissue was submerged in the formalin. Inks adhered securely and dried quickly without running or dripping into tissue crevices, remaining on the surface of the tissue. In addition, the inks did not migrate onto adjacent tissue margins. Ink colors were bright, easily identifiable, and easily distinguishable from one another.

Tissue is marked with the inks in accordance with the invention may be processed with methods known to those of skill in the art. An exemplary method of processing tissue for visualization under a microscope is shown in Table XI.

TABLE XIII

| | |
|---|---|
| 10% Formalin | 24-48 Hours |
| 70% ETOH | 1 Wash/30 Minutes |
| 90% ETOH | 2 Washes/30 Minutes Each |
| 100% ETOH | 2 Washes/30 Minutes Each |
| Xylene | 3 Immersions/60 Minutes Each |
| Paraffin | 2 Baths/60 Minutes Each |

The tissue specimens are cut on a microtome and stained with Gills hematoxylin and Eosin Y and are viewed under a microscope at 2.5× and 60× magnification. The inks are easily viewed under a microscope. The inks form an opaque film or shell on the tissue specimen outer surface with greater adherence to the tissue than commercially available inks. The ink colors are bright, easily identifiable, and easily distinguishable from one another.

The fixing solution composition according to the present invention includes 95% ethanol, lactic acid, deionized water and formalin. Preferred ranges of the foregoing are set forth in the table below.

TABLE XIV

FIXING SOLUTION FORMULATION

| Ingredient | Target Formulation | Preferred Range |
|---|---|---|
| Ethanol 95% | 33.33% | 31.0-35.0% |
| Lactic Acid | 11.11% | 10.1-12.1% |
| Deionized Water | 33.33% | 31.3-35.3% |
| Formalin | 22.22% | 21.0-23.0% |

Preparation of Fixing Solution

Example 1

Fixing solution is sometimes sprayed, dabbed, dripped, or otherwise applied onto the inked tissue to enhance the adherence of the ink to the tissue. The fixing solution is prepared by first mixing 31.5 wt. % of water with 34.5% wt. % ethanol (95%) in a clean stainless steel vessel. Lactic acid in an amount of 11.5 wt. % is added followed by 22.5 wt. % formalin while mildly stirring the mixture for twenty to thirty minutes after which is it ready to use. The fixing solution in accordance with the invention enhances the adherence of the ink to the tissue as best seen in FIG. XX In addition, the fixing solution prepared as illustrated in this Example does not have an odor that was offensive or pungent.

Example 2

A second batch of fixative is prepared by first mixing 33.33 wt. % of deionized water with 33.33% wt. % ethanol (95%) in a clean glass lined vessel. Lactic acid in an amount of 11.11 wt. % is added followed by 22.22 wt. % formalin while mildly stirring the mixture for twenty to thirty minutes after which is it ready to use. The fixative in accordance with the invention enhances the adhesion of the inks to the tissue. In addition, fixative prepared as illustrated in this Example does not have an odor that is offensive or pungent.

Inks prepared in accordance with the invention need no further dilution and are ready to be applied directly to tissue specimens. When three inks are placed on a tissue specimen the inks do not bleed onto adjacent margins and are readily visible and distinguishable from each other under a microscope.

Although the present invention has been described with reference to certain aspects and embodiments, those of ordinary skill in the art will appreciate that changes may be made in form and detail without departing from the spirit and scope of the invention.

We claim:

1. An ink composition for marking a tissue specimen comprising:
   30.0 wt. % to 54.0 wt. % of an alkali soluble styrene;
   0.3 wt. % to 1.7 wt. % cellulose;
   8.0 wt. % to 48.0 wt. % colorant;
   0.0% to 13.0 wt. % pigment;
   23.0 wt. % to 47.0 wt. % solvent; and
   0.35 wt. % to 1.65% of a defoamer,
   wherein said ink composition has a viscosity of from 90 ku to 115 ku at room temperature and a reflective light value in the L.a.b. color space in dimension L of from approximately 31.4 to 84.51, in dimension a of from approximately −42.32 to +52.81, and in dimension b of from approximately −30.73 to +88.09.

2. The ink composition of claim 1 further comprising 0.05 wt. % to 0.15 wt. % of an amine.

3. The ink composition of claim 2 wherein the amine is amino-2-methyl-1-propanol 95% active (5% water).

4. The ink composition of claim 1 wherein the cellulose is selected from ethyl hydroxyethyl cellulose and methyl ethyl hydroxyethyl cellulose.

5. The ink composition of claim 4 wherein the cellulose is ethyl hydroxyethyl cellulose.

6. The ink composition of claim 1 wherein the ink composition has a peak transmission in the UV-visible light spectrum at a wavelength of from 322 nm to 716 nm.

7. The ink composition of claim 1 further comprising a preservative in an amount from 0.1 to 1.1 wt. %.

8. The ink composition of claim 1 wherein the alkali soluble styrene is an acrylic styrene copolymer emulsion.

9. The ink composition of claim 7 wherein said preservative comprises an amount from 0.2 to 1.0 wt. %.

10. The ink composition of claim 1 wherein the solvent comprises deionized water.

11. The ink composition of claim 1 wherein the colorant comprises from 7.59 to 11.59 wt. % carbazole violet and the pigment comprises 2.75% to 4.75 wt. % white mica.

12. The ink composition of claim 11 wherein said ink composition has a peak transmission in the UV-visible light spectrum at a wavelength of 451 nm.

13. The ink composition of claim 1 wherein the colorant comprises from 24.48 to 28.48 wt. % phtahalo green yellow and the pigment comprises 8.6 to 10.6 wt. % white mica.

14. The ink composition of claim 13 wherein said ink composition has a peak transmission in the UV-visible light spectrum at a wavelength of 545 nm.

15. The ink composition of claim 1 wherein the colorant comprises from 21.28 to 25.28 wt. % phthalo blue green and the pigment comprises 6.53 to 8.53 wt. % white mica.

16. The ink composition of claim 15 wherein said ink composition has a peak transmission in the UV-visible light spectrum at a wavelength of 506 nm.

17. The ink composition of claim 1 wherein the colorant comprises from 15.18 to 19.18 wt. % naphthol red and the pigment comprises 4.40 to 8.40 wt. % quinacridone red.

18. The ink composition of claim 17 wherein said ink composition has a peak transmission in the UV-visible light spectrum at wavelengths of 449 nm and 716 nm.

19. The ink composition of claim 1 wherein the colorant comprises from 4.22 to 8.22 wt. % benzimidazolone yellow, 4.16 to 8.16 wt. % disazopyrazolone orange and the pigment comprises 1.5 to 3.5 wt. % white mica.

20. The ink composition of claim 19 wherein said ink composition has a peak transmission in the UV-visible light spectrum at wavelengths of 352 nm and 636 nm.

21. The ink composition of claim 1 wherein the colorant comprises from 25.63 to 29.63 wt. % benzimidazolone yellow.

22. The ink composition of claim 21 wherein said ink composition has a peak transmission in the UV-visible light spectrum at wavelengths of 322 nm and 605 nm.

23. The ink composition of claim 1 wherein said ink composition has two peak transmissions in the UV-visible light spectrum at wavelengths from 322 nm to 716 nm.

24. The ink composition of claim 1 wherein said ink composition has a single peak transmission in the UV-visible light spectrum at a wavelength from 451 nm to 545 nm.

25. The ink composition of claim 1 wherein said ink composition is gamma irradiated with a minimum dose of 27.5 kGy up to a maximum dose of 45 kGy.

26. The ink composition of claim 25 wherein said ink composition is gamma irradiated with a minimum dose of 31.0 kGy to a maximum dose of 39 kGy.

27. The ink composition of claim 26 wherein said ink composition is gamma irradiated with a dose of 33 kGy.

28. The ink composition of claim 1 wherein the colorant comprises from 9.79 wt. % to 13.79 wt. % benzimidazolone yellow and from 0.36 wt. % to 4.36 wt. % disazopyrazolone orange and from 5.72 wt. % to 9.72 wt. % orange.

29. The ink composition of claim 28 wherein said ink composition has two peak transmission in the UV-visible light spectrum at wavelengths from 475 nm to 675 nm.

30. An ink composition comprising:
  30.0 wt. % to 54.0 wt. % of an alkali soluble styrene;
  0.3 wt. % to 1.7 wt. % cellulose;
  8.0 wt. % to 48.0 wt. % colorant;
  0.0% to 13.0 wt. % pigment;
  23.0 wt. % to 47.0 wt. % solvent; and
  0.35 wt. % to 1.65% of a defoamer in combination with a fixing solution having a composition of from 31.0-35.0% ethanol (95%), 10.1-12.1% lactic acid, 31.3-35.3% deionized water and 21.0-23% formalin.

31. An ink composition for marking tissue comprising:
  30.0 wt. % to 54.0 wt. % of an alkali soluble styrene;
  0.3 wt. % to 1.7 wt. % cellulose;
  from 15.6 wt. % to 19.60 wt. % lampblack colorant;
  0.0% to 13.0 wt. % pigment;
  23.0 wt. % to 47.0 wt. % solvent; and
  0.35 wt. % to 1.65% of a defoamer, wherein said ink composition has a viscosity of from 90 ku to 115 ku at room temperature and a reflective light value in the L.a.b. color space in dimension L of 25.81, in dimension a of −0.02, and in dimension b of −0.49.

32. The ink composition of claim 31 wherein said ink composition has a lineal UV-Vis spectrum having no visible peak transmission between 250 nm and 950 nm.

33. A method of preparing an ink composition for use in marking tissue specimens comprising:
  preparing a first solution including mixing from 0.3 wt. % to 1.7 wt. % ethyl hydroxyethyl cellulose into 23.0 wt. % to 47.0 wt. % deionized water under agitation;
  adding from 0.05 wt. % to 1.05 wt. % of amino-2-methyl-1-propanol (95% active, 5% water);
  allowing said first solution to sit at room temperature for 5 to 12 hours;
  preparing a final solution by mixing from 30.0 to 54.0 wt. % alkali soluble styrene acrylic resin, 0.35 to 1.65 wt. % defoamer, 8.0 to 35.0 wt. % colorant, 0.0 to 13.0 wt. % pigment to said first solution;
  at room temperature measuring a viscosity of said final solution and adjusting said viscosity with methyl ethyl hydroxyethyl cellulose until a desired range of from 90 ku to 115 ku is reached.

* * * * *